(12) United States Patent
Hinssen et al.

(10) Patent No.: US 6,356,789 B1
(45) Date of Patent: Mar. 12, 2002

(54) MEDICAL INFORMATION DEVICE

(75) Inventors: Hans-Josef Hinssen, Anröochte/Altenmellrich; Heinz Michael Zollner, Paderborn, both of (DE)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 09/182,190

(22) Filed: Oct. 30, 1998

(51) Int. Cl.[7] ............................................. A61N 1/02
(52) U.S. Cl. ................................................ 607/60
(58) Field of Search ....................... 607/30, 32, 59, 607/60

(56) References Cited

U.S. PATENT DOCUMENTS

| | | | |
|---|---|---|---|
| 5,606,978 A | 3/1997 | Armstrong et al. | 128/711 |
| 5,669,393 A | 9/1997 | Faisandier | 128/710 |
| 5,722,999 A * | 3/1998 | Snell | 607/32 |
| 5,752,976 A * | 5/1998 | Duffin et al. | 607/32 |
| 5,800,473 A | 9/1998 | Faisandier | 607/59 |
| 5,832,488 A | 11/1998 | Eberhardt | 707/10 |

FOREIGN PATENT DOCUMENTS

GB    EP0773 038 A2    5/1997

OTHER PUBLICATIONS

Deficard — Orga Kartensysteme GmbH.
Orga Searches For Smart Card Success—Card Technology, Nov/Dec. 1997, pp. 57–60.

* cited by examiner

Primary Examiner—William E. Kamm
(74) Attorney, Agent, or Firm—Thomas F. Woods; Michael J. Jaro; Thomas G. Berry

(57) ABSTRACT

Described is a data processing unit for the telemetric adjustment of an implant and for telemetric communication between the implant and a data device. The data device comprises a control unit for processing the data entered, a memory unit for saving the data supplied, an entry unit for entry of data, a display unit for display of data, a telemetry unit for transfer of data to the implant or vice versa; and at least one reading device to read and/or write on a first and second data carrier, whereby, on the first data carrier, one can store the status data transferred to the implant, and, on the second data carrier, the administrative data pertaining to the implant.

12 Claims, 1 Drawing Sheet

MEDICAL INFORMATION DEVICE

DESCRIPTION (SPECIFICATION)

The invention pertains to a data processing unit for the telemetric adjustment of an implant and/or for telemetric communication between the implant and a data device.

It is already known that the technical data of an implant and the patient-dependent data about the patient's clinical history can be stored on a chip card so that the respective treating physician has the current data available at each followup examination occurring after implantation. The corresponding data are manually entered into a data device and are stored on the chip card via a card reading device connected to the data device. The reading of the data from the chip card occurs in the reverse direction.

Disadvantageously for data transfer in known processing is that no automatic storage of the data occurs on a data carrier to be handed over to the patient. Automatic followup of the implant between the clinic medium and the implant manufacturer is not provided.

In addition, it is known that implants such as, for example, pacemakers are telemetrically adjusted, and the corresponding status data are read out of the implant.

The problem for the invention is therefore to construct a data processing unit for telemetric adjustment of the implant and/or for telemetric communication between the implant and a data device in such a way that simplified and improved processing of the patient-based data (status data from the implant) is made possible, as well as provision of implant-based data (administrative data from the implant).

For the solution to this problem, the invention has the characteristics of claim 1.

The data processing unit in accordance with the invention permits, in a simple way, the provision of data stored on a portable data carrier, whereby medical or technical status data content is stored on a first data carrier for delivery to the patient and whereby implant-based administrative data about the implant are stored on a second data carrier in order to remain in the data device or for delivery to an authorized person. The administrative data can preferably contain followup information which can be regularly read out by a representative of the implant manufacturer. Rapid access to the current adjustment data of the implant and optionally in addition to the patient data is made possible for the treating physician.

All patient-relevant data can advantageously be stored on the first data carrier whereby, in addition, measurement data which have been determined by cyclic measurements of the implant itself can then be compared with previous patient data stored on the data carrier which represent a previous time interval, and evaluated during a followup examination of the patient. This evaluation preferably occurs in the data device.

The second data carrier collects the administrative data of several implants and thereby permits a defined and physically separate compilation of the implants for subsequent evaluation of the same at a fixed location. One thereby ensures via the control program implemented in the data device that only administrative data are stored on the second data carrier and that only the current status data, in the first data carrier.

The invention permits the automatic storage of relevant data (status data, administrative data) in the first or second data carrier.

The administrative data of an implant are preferably stored in the first data carrier and are transferred to the second data carrier by means of a control program immediately after implantation or on the occasion of initially writing on the first data carrier, and stored there. The data are thereby temporarily stored on the data carrier. These accumulating administrative data about the implants can then be read from the second data carrier at defined intervals by an authorized person for followup purposes and further processed. The data carrier advantageously serves for control of the communication or for mediating during communication between the first and second data carrier as well as between these and the implant.

One single data device advantageously serves for processing the data, whereby the status data and the administrative data are stored in different or temporary memory regions. Communication between the data device and the implant is made possible by means of the presence of a telemetry unit whereby current or new data can be rapidly stored on the corresponding data carriers.

According to a further development of the invention, the data device has a card reading device to which two chip cards are assigned for the memory of status data, on the one hand, and administrative data on the other hand. The card reading device preferably has a PCMCIA interface so that it is integrated into the data device in a space saving manner.

The data device is advantageously constructed as a portable data carrier (laptop) and the card reader as the PCMCIA card reader with a receptacle for a chip card in standard size (credit card size), on the one hand, and with a receptacle for a chip card in minichip card format (GSM card) on the other hand. Herewith, the presence of a second large volume card slot is avoided.

In addition, the problem which is the basis of the invention is to indicate a process for processing the data between a data device and an implant so that data processing and data evaluation are improved.

For the solution of the problem, the process in accordance with the invention has the characteristics of claim 9.

The advantage of the process is to be seen in that the status data and the administrative data are processed independently of each other in the data device and are stored according to the requirements of the respective data carrier. Herewith, the data existing in the portable data carrier in safeguarded form can be removed from the data device and optionally supplied to an additional data device for further processing of the data.

An embodiment example of the invention will be explained in more detail below on the basis of the drawings.

The data processing unit can be used for processing data from any implantable medical device. By way of example is the processing of data provided in pacemaker systems, defibrillators or neurostimulators. This data processing unit is preferably used with implants which must be checked or readjusted at regular intervals.

Figure 1:
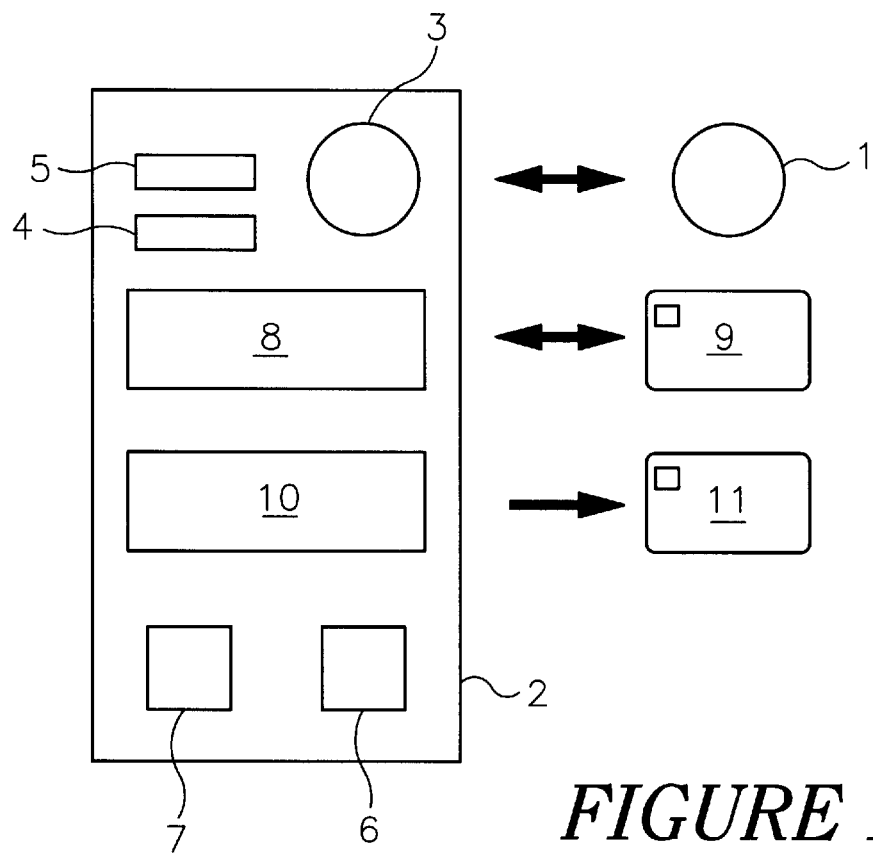
FIG. 1 shows a block circuit diagram of a data processing unit.

FIG. 1 shows a block circuit diagram of a data processing unit for a pacemaker as implant 1 which is equipped with a control unit which is not illustrated for control of the electrical impulses released in the cardiac region via an electrode. The impulses have a series of parameters, such as, e.g., impulse width or impulse height, which are specified by the control unit of the implant 1. The control of the impulses takes place as a function of the additional adjustment parameters in order to ensure adaptation based on the medical findings of the patient.

The control unit of implant 1 has a coil which is not illustrated as the antenna for communication with an external data device 2, whereby the coil can be used in connection with the telemetry unit 3 of the data device 2 for transfer of data in one or the other direction. The telemetry unit 3 also has a coil as an antenna.

For entry of the data transmitted via telemetric transfer to the implant 1, the data device 2 has an entry unit 4 which is preferably constructed as a keyboard. The data entered are shown on a display unit 5 for checking. The display unit 5 can be constructed as an LC display or as the monitor of a personal computer or laptop. This display unit 5 also serves for presentation of the corresponding data which can be read from the implant 1.

The data device 2 has a control unit 6 and a memory unit 7, whereby the control unit 6 is controlled by a program which processes the data entered, especially the status data required for the adjustment of the implant 1, and temporarily stores it in memory unit 7. The control unit 6 then supplies the status data to the telemetry unit 3 for transfer to the implant 1. Both the control unit 6 and the implant 1 have a microprocessor for processing the data. The telemetry unit 3 is advantageously integrated into the data device 2 so that the data device 2 has a compact structure and is advantageously held in the vicinity of the implant 1 as the portable data device 2 during the transfer time.

The implant 1 has a memory such that, on the one hand, implant-based and unchangeable data like the so-called administrative data, and, on the other hand, patient-based data can be stored. The patient-based data consist of unchangeable data such as the patient's code and birth date, on the one hand, and, on the other hand, status data changeable by the physician. The changeable status data are either adjustment parameters of the implant changeable by the physician, or measurement data about the patient's clinical state.

The data device 2 also has two card reading devices, whereby the first card reading device 8 corresponds to a first chip card (patient card) 9 and the second card reading device 10 to a second chip card (followup card) 11. The patient card 9 serves for storing the medical status data of the implant 1 and is handed out to the patient after implantation. The patient carries this patient card 9 with him as identification as it were and presents it to the treating physician at the next examination. By insertion of the patient card 9 into the first card reading device 8 and running a software supported routine, it is possible to display the current status data in the display unit 5 or to print it out by means of a connected printer. If required, the status data can be changed on the basis of medical findings, whereby the changed status data are transferred as current status data for the adjustment of the implant 1, on the one hand, and, on the other hand, are stored on the patient card 9.

The control unit 6 of the data device 2 permits the selective connection or, data transfer from the entry unit 4 or the telemetry unit 3 to or from the patient card 9, on the one hand, or the followup card 10 on the other hand. Thus the current status data can be read off the patient card 9 and supplied to the display unit 5 or a connected printer as an output unit. In addition, current status data entered via the entry unit 4 can be stored on the patient card 9.

Manufacturer-specific data are also preferably stored in the patient card 9 as administrative data like, by way of example, the name of the manufacturer of the implant, the model type of the implant, the serial number, the battery status of the implant as well as the status of the pacemaker programming. Besides the contact surface, below which the chip is embedded in the card material, the surface of the patient card 9 also has typographically applied information about the implant or the manufacturer. The other surface can serve as an advertising carrier.

According to one embodiment of the invention, the patient specific status data from the implant 1 can also be automatically stored on the patient card 9 via an appropriate control program. In this way, the treating person needs only to enter the implant-relevant data for adjustment of the implant 1, whereby these are supplied to the patient card 9 after examination of the correct saving of the status data in the implant 1. Hereby, one ensures that only the data supplied to the implant are saved on the patient card 9 and no data entry occurs from interchange of the patient data.

According to a preferred embodiment of the invention, the administrative data stored on the patient card 9 are written just once on the followup card 10, namely after initially writing on the patient card 9, by means of a control program stored in the memory unit 7. This followup card 10 is preferably permanently connected with the data device 2 and collects the administrative data from a number of patient cards 9 written on by the data device 2. Hereby, by means of running a single control program, the status data can be written to the patient card 9 on the one hand, and the administrative data to the followup card 10 of the corresponding implant 1 on the other hand.

Alternatively, the administrative data can also be stored on the followup card 10 immediately after the initial entry of the status data in the data device 2. Hereby, one ensures that the followup card 10 is written prior to issuing the patient card 9 so that followup of the implant 1 is ensured. The control program has means such that one ensures that the administrative data for an implant 1 are stored only once in the followup card 10.

The followup card 11 is assigned to the data device 2 and remains in the inserted state, in contrast to patient card 9. The data characterizing the implant 1 such as, for instance, the serial number, are stored on the followup card 10 as administrative data upon undertaking the implantation. It allows the administrative data to be called up rapidly and reliably at regular intervals by a representative of the implant manufacturer without the administrative process of the clinic being disturbed. The administrative data preferably serve for followup of the implant 1 with the clinic administration. The administrative data are originally stored in the implant 1 and are written onto the followup card 11 via temporary storage of the same in the data device 1.

Figure 2:
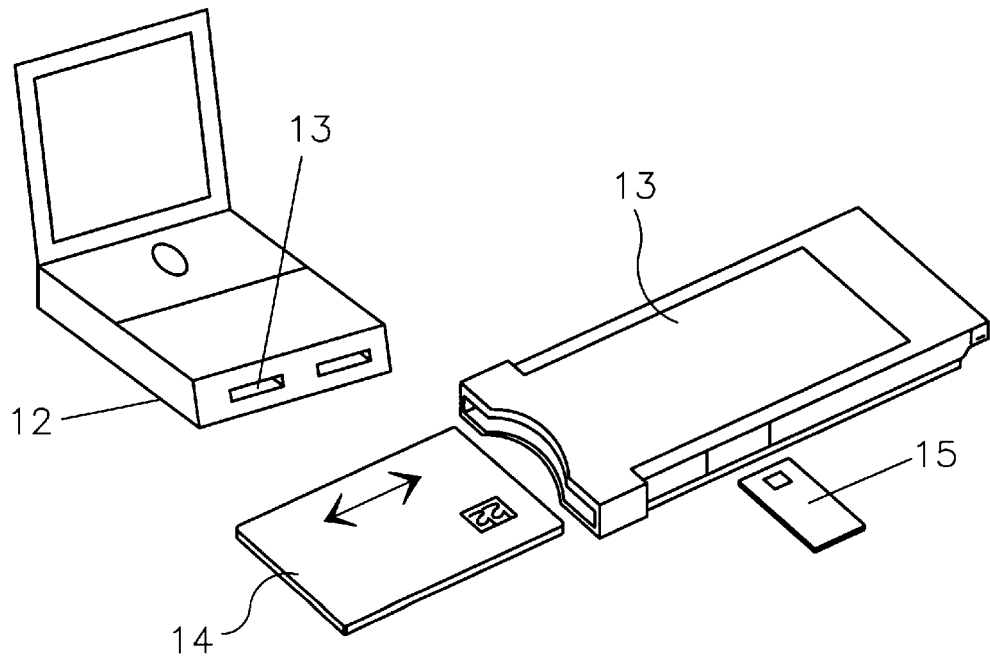
FIG. 2 shows one form of embodiment of a data device.

According to an embodiment of the invention in accordance with FIG. 2, a data device is constructed as a conventional commercial notebook 12 which is equipped with a PCMCIA card reading device 13. The PCMCIA card reading device 13 is suitable for accommodating a credit card size patient card 14 and a minichip card size followup card 15 in a space-saving manner. Since the followup card 15 must only rarely be removed from the data device 12, it can be constructed as a plug-in card. Hereby, space-saving utilization of two cards is made possible.

Writing on the patient card 9 or the followup card 11 preferably occurs exclusively in connection with the data device 2. This is achieved by means of an authentication process carried out by software, in which the identification of the patient or followup card, on the one hand, and that of the data device, on the other hand, are examined. If the legitimacy of the card is established via a comparison (for instance, by entry of a PIN), then data exchange can occur. Otherwise, communication to or from the card cannot be arranged.

What is claimed is:

1. An external data device for programming and storing information relating to an implantable medical device, comprising:
   (a) means for entering administrative data into the external data device;
   (b) means for displaying data operatively coupled to the entry means;
   (c) mean s for telemetrically communicating with implantable medical device and for sending data to and receiving patient status data from the implantable medical device;
   (d) a control unit for processing the entered, sent or received data, the control means being operatively connected to the telemetry means;
   (e) a memory unit, operatively coupled to the control unit, for storing the entered, sent or received data;
   (f) a first reading device operatively connected to the control unit and configured to at least one of read patient data from and write patient data to a first data carrier, the first data carrier being transportable and removable from the first reading device, and
   (g) a second reading device operatively connected to the control unit and configured to at least one of read administrative data from and write administrative data to a second data carrier, the second data carrier being permanently connected to the second reading device.

2. The external data device of claim 1, wherein the memory unit further comprises a first memory region for storing patient status data and a second memory region for storing administrative data.

3. The external data device of claim 1, wherein the second reading device further comprises means for at least one of reading initial patient status data from and writing initial patient status data to the second reading device.

4. The external data device of claim 1, wherein the first reading device is a card reading device and the first data carrier is a chip card comprising a microprocessor.

5. The external data device of claim 4, wherein the card reading device is integrated into the external data device as a PCMCIA interface.

6. The external data device of claim 4, wherein software-based functions stored in the implantable medical device may be activated by means, integral to the external data device, for generating an activation signal, the software-based functions being stored as administrative data on the second data carrier when the activation signal is generated.

7. The external data device of claim 6, further comprising means for at least one of revising and expanding the software-based functions stored in the implantable medical device when the activation signal is generated.

8. The external data device of claim 1, wherein the second data carrier comprises means for storing administrative data from a plurality of implant procedures.

9. The external data device of claim 1, further comprising means for updating the patient status data and transferring same to the implantable medical device for storage therein and to the first data carrier for storage thereon, and means for storing the administrative data on the second data carrier as soon as the patient status data are stored for the first time in one of the memory unit and the first data carrier.

10. The external data device of claim 1, further comprising means for transferring and storing the administrative data in another external data device when the administrative data are stored for the first time on the second data carrier.

11. The external data device of claim 1, further comprising means for transferring the administrative data to the second data carrier and storing same thereon when the first data carrier is initially used to store patient status data thereon.

12. The external data device of claim 1 further comprising means for storing the patient status data in the implantable medical device first, followed by storing the patient status data on the first data carrier.

* * * * *

UNITED STATES PATENT AND TRADEMARK OFFICE
CERTIFICATE OF CORRECTION

PATENT NO. : 6,356,789 B1
DATED : March 12, 2002
INVENTOR(S) : Hans-Josef Hinssen et al.

It is certified that error appears in the above-identified patent and that said Letters Patent is hereby corrected as shown below:

Column 5,
Line 9, after "(c)" delete "mean s for" and insert -- means for --.

Signed and Sealed this

Thirteenth Day of June, 2006

JON W. DUDAS
*Director of the United States Patent and Trademark Office*